(12) United States Patent
Hamer et al.

(10) Patent No.: US 9,623,603 B2
(45) Date of Patent: Apr. 18, 2017

(54) METHOD OF MAKING A CONDUIT FOR INTERVENTIONAL PROCEDURES

(71) Applicant: W. L. Gore & Associates, Inc., Newark, DE (US)

(72) Inventors: Rochelle M. Hamer, Flagstaff, AZ (US); Eric Gerard Johnson, New Albany, IN (US); Stanislaw L. Zukowski, Flagstaff, AZ (US)

(73) Assignee: W. L. Gore & Associates, Inc., Newark, DE (US)

( * ) Notice: Subject to any disclaimer, the term of this patent is extended or adjusted under 35 U.S.C. 154(b) by 471 days.

(21) Appl. No.: 14/255,599

(22) Filed: Apr. 17, 2014

(65) Prior Publication Data

US 2014/0224404 A1    Aug. 14, 2014

Related U.S. Application Data

(63) Continuation of application No. 11/246,592, filed on Oct. 7, 2005, now abandoned.

(51) Int. Cl.

| A61M 25/00 | (2006.01) |
|---|---|
| B29C 65/00 | (2006.01) |
| A61F 2/954 | (2013.01) |
| A61M 25/06 | (2006.01) |
| A61F 2/06 | (2013.01) |
| A61M 39/06 | (2006.01) |

(52) U.S. Cl.
CPC .............. *B29C 66/63* (2013.01); *A61F 2/954* (2013.01); *A61M 25/0662* (2013.01); *B29C 66/51* (2013.01); *A61F 2002/061* (2013.01); *A61F 2002/065* (2013.01); *A61F 2250/0039* (2013.01); *A61M 25/0032* (2013.01); *A61M 39/0693* (2013.01); *A61M 2025/0034* (2013.01); *Y10T 156/10* (2015.01)

(58) Field of Classification Search
CPC .. A61M 2025/0188; A61M 2025/0037; A61M 25/0026
USPC .......................................................... 156/187
See application file for complete search history.

(56) References Cited

U.S. PATENT DOCUMENTS

| 4,922,905 A | | 5/1990 | Strecker | |
|---|---|---|---|---|
| 5,195,962 A | * | 3/1993 | Martin | ................ A61M 25/001 604/43 |
| 5,263,932 A | | 11/1993 | Jang | |
| 5,554,118 A | | 9/1996 | Jang | |
| 5,571,094 A | | 11/1996 | Sirhan | |
| 6,007,517 A | | 12/1999 | Anderson | |
| 6,142,973 A | | 11/2000 | Carleton et al. | |
| 6,827,710 B1 | | 12/2004 | Mooney et al. | |

(Continued)

FOREIGN PATENT DOCUMENTS

| EP | 0 897 700 | 2/1999 |
|---|---|---|
| EP | 1 634 615 | 3/2006 |

(Continued)

*Primary Examiner* — Scott W Dodds
(74) *Attorney, Agent, or Firm* — Paul J. Fordenbacher, Esq.

(57) ABSTRACT

A conduit, such as an introducer sheath, catheter, or guide catheter, incorporating two or more separate lumens to prevent the entanglement of guidewires located at least partially within the conduit. The lumens are separated by at least one disruptable barrier that allows multiple lumens to be converted into fewer lumens prior to or as a device is advanced through the introducer sheath.

13 Claims, 19 Drawing Sheets

(56) References Cited

U.S. PATENT DOCUMENTS

| | | |
|---|---|---|
| 6,884,258 B2 | 4/2005 | Vardi et al. |
| 2005/0033239 A1 | 2/2005 | Argentine |
| 2012/0101480 A1* | 4/2012 | Ingle ................ A61M 25/0009 |
| | | 604/526 |

FOREIGN PATENT DOCUMENTS

| | | |
|---|---|---|
| WO | WO 01/37924 | 5/2001 |
| WO | WO 01/70299 | 9/2001 |
| WO | WO 02/091951 | 11/2002 |
| WO | WO 03/002020 | 1/2003 |
| WO | WO 03/079935 | 10/2003 |
| WO | WO 03/105922 | 12/2003 |

* cited by examiner

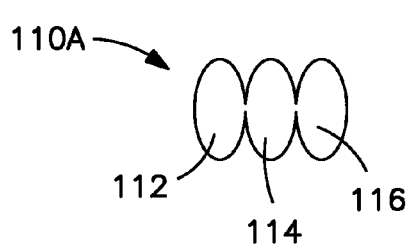
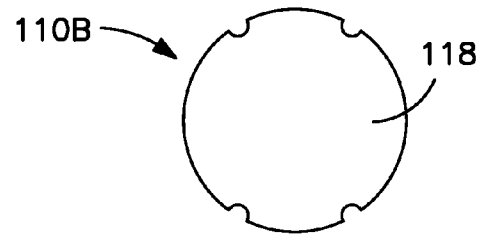
FIG. 17A  FIG. 17B
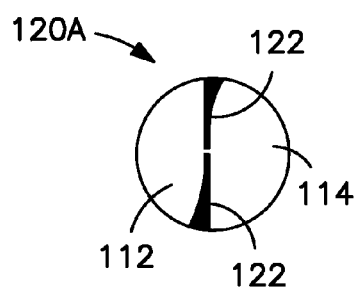
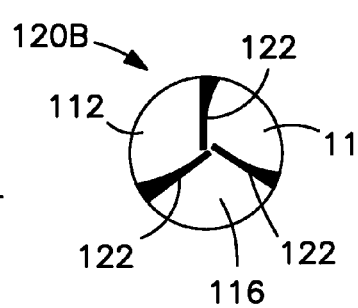
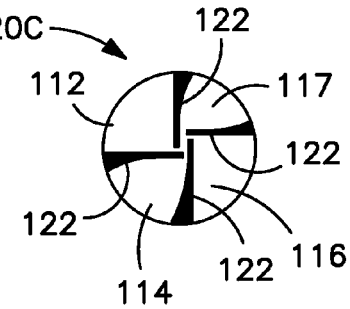
FIG. 18A  FIG. 18B  FIG. 18C
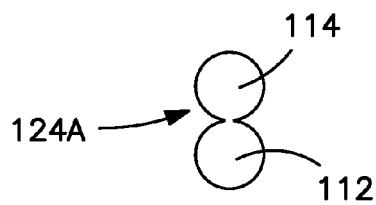
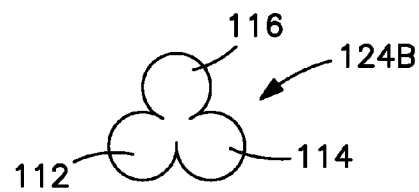
FIG. 19A  FIG. 19B
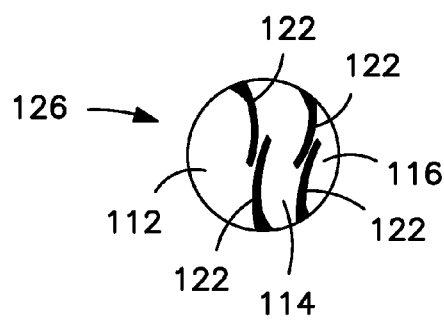
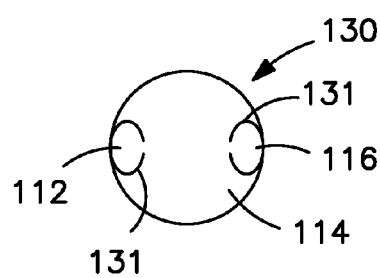
FIG. 20  FIG. 21

METHOD OF MAKING A CONDUIT FOR INTERVENTIONAL PROCEDURES

BACKGROUND

Field of the Invention

Novel conduits, such as guide catheters and catheter introducer sheaths, for use in interventional procedures, particularly introducer sheaths adapted for use with multiple guidewires.

Description of Related Art

It is often desirable to use multiple guidewires in various endovascular procedures. For example when deploying stent graft aneurismal repair devices within branched vasculature, a first guidewire would be used to access the main artery while second and/or third guidewires would access the side branched arteries. Stent grafts with multiple guidewire ports would then be advanced along the respective guidewires and deployed at the desired sites. A common problem associated with the use of multiple guidewires is the "crossing" or entanglement of the guidewires in the vasculature proximal to the treatment site. Crossed and entangled guidewires prohibit or severely restrict the ability to advance a device with multiple guidewire ports to the treatment site. An introducer catheter or sheath is often employed to protect the vasculature from possible damage due to the advancement of the guidewires, catheters and subsequent devices but such use does not eliminate the occurrence of crossed guidewires. See for example U.S. Pat. No. 6,884,258 (to Vardi et al.) for a disclosure of problematic crossed guidewires.

SUMMARY

A method of manufacturing an introducer sheath in accordance with the present disclosure includes providing a mandrel extending along a longitudinal axis thereof and having a cylindrical outer surface, the mandrel having at least first and second sections each extending along the longitudinal axis; placing a film tubular member around one of the at least first and second sections of the mandrel; sandwiching a portion of the tubular member between the at least first and second sections, the portion of the tubular member defining a frangible barrier for an introducer sheath; extending a film layer about the mandrel, the film layer having an adhesive; curing the adhesive to form an introducer sheath having a frangible barrier; and removing the mandrel from the introducer sheath.

BRIEF DESCRIPTION OF THE DRAWINGS

FIG. 17A is an end view of a multi-lumen catheter having three lumens prior to expansion.

FIG. 17B is an end view of the catheter of 17A after expansion. The three lumen catheter of 17A has been converted into a single lumen catheter by the expansion.

FIGS. 18A through 18C depict catheters with interior barriers that can be disrupted. Once disrupted the catheter is converted into a catheter with a fewer number of lumens.

FIG. 19A is an end view of a catheter having two lumens that will transform into a single lumen catheter when expanded.

FIG. 19B is an end view of a catheter having three lumens that will transform into a single lumen catheter when expanded.

FIG. 20 is an end view of a catheter of the present invention. Shown is an end view of a catheter having four disruptable barriers that form three lumens. The three lumens can be converted into a single lumen when expanded.

FIG. 21 is an end view of a catheter of the present invention. Shown is a catheter having two disruptable barriers that form three lumens. Each barrier can have a slit (or other longitudinal opening) that can release the guidewires as a delivery catheter is advanced distally through catheter.

DETAILED DESCRIPTION

A better understanding of the present invention may be had with reference to the several figures.

Figure 1:
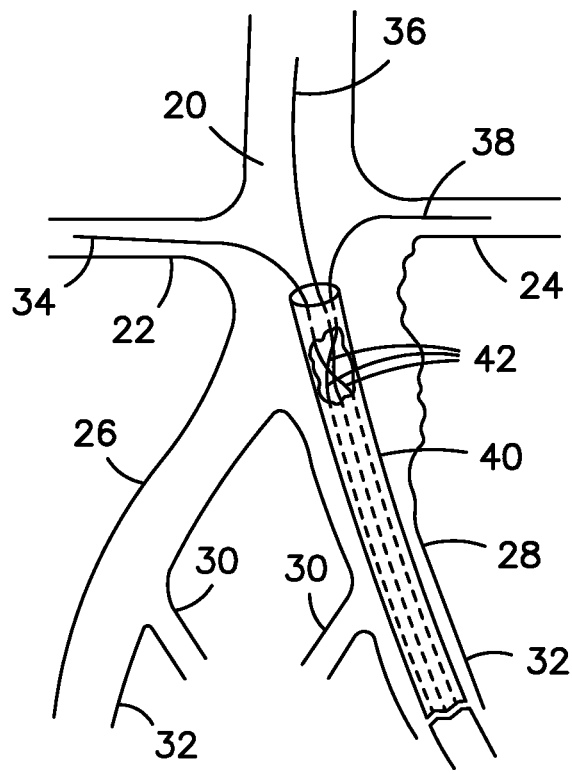
FIG. 1 is a schematic representation of the abdominal part of the aorta and its principal branches showing an introducer sheath and multiple guidewires of the current art.

Shown in FIG. 1 is a schematic representation of the abdominal part of the aorta and its principal branches. The abdominal aorta 20 is characterized by a right renal artery 22 and left renal artery 24. The large terminal branches of the aorta are the right and left common iliac arteries 26 and 28. Each common iliac artery branches into internal 30 and external 32 iliac arteries. An external iliac artery 32 becomes the femoral artery below the inguinal ligament. Internal iliac artery 30 is also known as the hypogastric artery. Additional vessels (e.g., second lumbar, testicular, inferior mesenteric, middle sacral) have been omitted for simplification. The infrarenal aorta is that portion of the aorta disposed between the renal arteries and the common iliac arteries. Throughout this application the term "distal" refers to the direction that is furthest away from the clinician or access site and the term "proximal" refers to the direction that is closest to the clinician or access site.

A typical procedure entails gaining initial femoral artery access percutaneously or with a surgical access. A floppy guidewire is then inserted into the artery past the treatment site to ensure access is maintained. An introducer sheath consisting of the outer sheath and an inner dilator is placed over the guidewire and into the vessel to the treatment site or as far as it will go. The dilator serves to both stiffen the sheath for pushability and to create a smooth transition between the relatively sharp end of the sheath and the tissue. The floppy guidewire is switched out for the appropriate stiff guidewire using the sheath to maintain arterial access. The dilator is then removed and the treatment device is then guided over the guidewire and deployed.

As shown in FIG. 1, first, second and third guidewires 34, 36, 38 have been positioned within the main aorta 20 and within the two renal arteries 22, 24. The guidewires have been positioned with the aid of a single lumen introducer sheath 40 according to the current art. As depicted in the cut away portion of the introducer sheath, the three guidewires 34, 36, 38 are "crossed" 42 and entangled within the introducer sheath. The crossed and entangled guidewires prohibit or severely restrict the ability to advance devices, and particularly multi-lumen devices, to the treatment site.

Figure 2A:
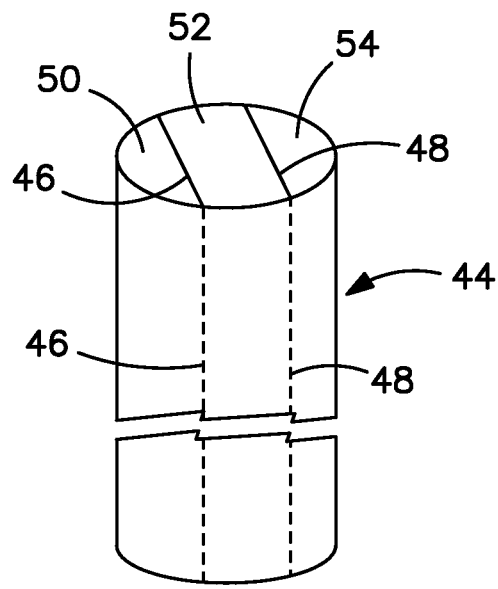
FIG. 2A is a partial, mid-section perspective view of a multi-lumen introducer sheath according to a preferred embodiment of the present invention.

FIG. 2A is a partial, mid-section perspective view of a multi-lumen introducer sheath according to an aspect of the present invention. Shown is an introducer sheath portion 44 having two distruptable barriers 46, 48 that can extend through a substantial length (or the entire length) of the introducer sheath 44. The two disruptable barriers 46, 48 form first, second and third lumens 50, 52, 54 that can extend through a substantial length (or the entire length) of the introducer sheath 44. Typical hemostatic valves, radiopaque markers and sheath distal tip details have been omitted for clarity.

Figure 2B:
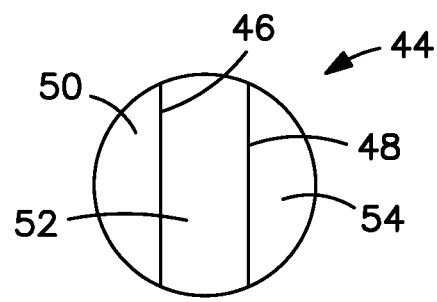
FIG. 2B is an end view of the introducer sheath of FIG. 2A. Shown are two disruptable barriers that form three lumens within the introducer sheath.

Shown in FIG. 2B is an end view of the introducer sheath 44 of FIG. 2A. Shown are the two disruptable barriers 46, 48 that form three lumens 50, 52, 54 within the introducer sheath 44.

FIGS. 3 through 14 depict an operational procedure used to repair an aortic aneurysm that includes the deployment of three stent grafts. The first stent graft is deployed across the main body of the aorta adjacent to the two renal arteries. The second and third stent grafts are then guided through "side branch" openings within the main stent graft and are then deployed within the renal arteries.

Figure 3:
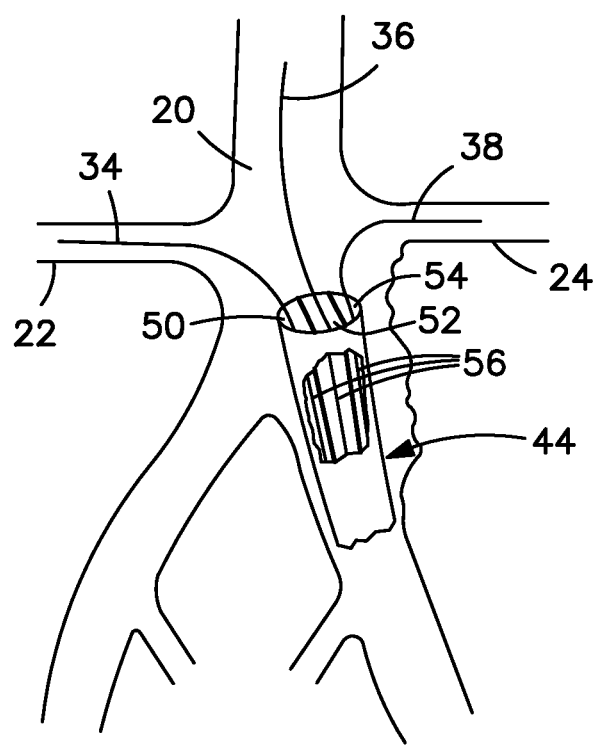
FIG. 3 is a partial perspective view of a distal portion of an introducer sheath according to the present invention. Shown are three guidewires positioned within the aorta and within the two renal arteries.

FIG. 3 is a schematic representation of the abdominal part of the aorta and its principal branches. Included is a partial perspective view of a distal portion of an introducer sheath 44 according to an aspect of the present invention. Shown are three guidewires 34, 36, 38 positioned within the aorta 20 and within the two renal arteries 22, 24. The guidewires have been positioned with the aid of a three lumen introducer sheath 44 according to an aspect of the present invention. Each guidewire is contained within a separate lumen within the introducer sheath. As depicted in the cut away portion of the introducer sheath, the three guidewires 34, 36, 38 are separated 56 and prevented from being "crossed" as a result of the three separate lumens.

Figure 4:
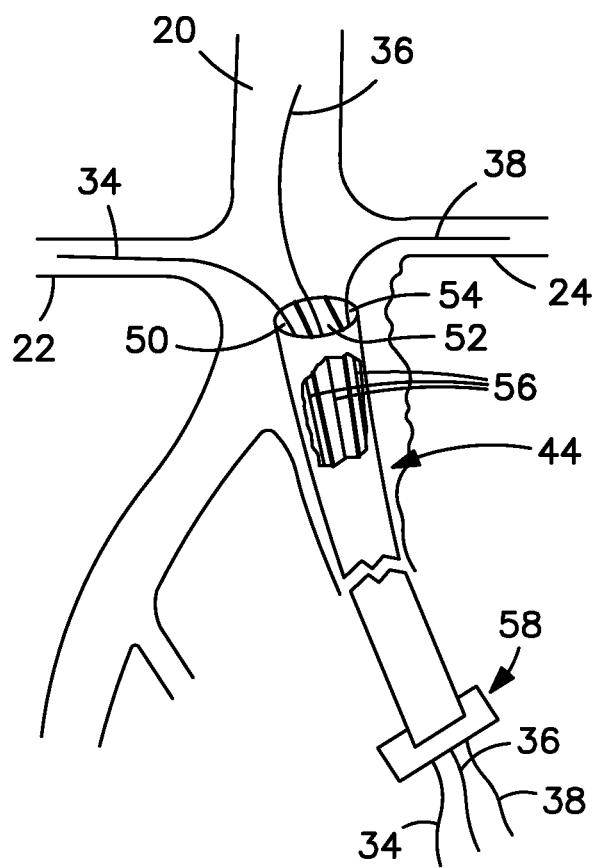
FIG. 4 is a perspective view of an introducer sheath according to the present invention. Shown are the proximal ends of three guidewires projecting from the proximal hub assembly.

FIG. 4 is a schematic representation of an aortic section with a perspective view of an introducer sheath 44 according to the present invention. Shown is an introducer sheath 44 with three separate lumens 50, 52, 54. Three guidewires 34, 36, 38 are shown, each guidewire being contained within one of the three separate lumens. The three guidewires are positioned distally into the main portion of the aorta and into two renal arteries. The proximal ends of the three guidewires project from the proximal hub assembly 58. The proximal hub assembly contains a hemostatic valve assembly that minimizes or prevents back-bleeding while also allowing advancement of guidewires and subsequent devices. Additional hubs and connectors, for example flushing hubs, have been omitted for clarity.

Figure 5:
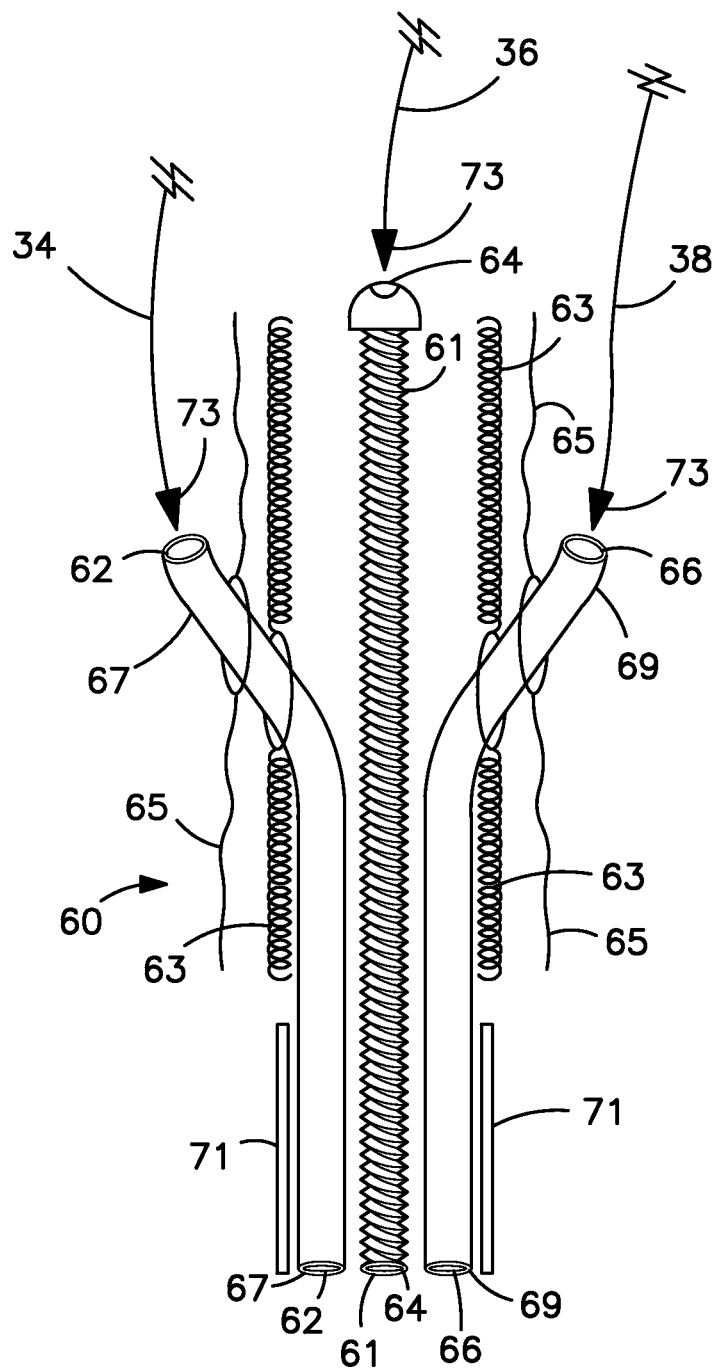
FIG. 5 is a partial cross-sectional schematic view of a distal end of a stent delivery system that is compatible with an introducer sheath of the present invention.

FIG. 5 is a partial cross-sectional schematic view of a distal end of a stent delivery system 60 that is compatible with an introducer sheath of the present invention. Shown is a catheter 71, containing two guidewire tubes 67, 69 along with a central catheter shaft 61. The guidewire tubes 67, 69 have guidewire lumens 62, 66. The central catheter shaft 61 has a guidewire lumen 64. All four components 61, 71, 67, 69 extend to the proximal hub (not shown).

A self expanding main body stent or stent graft (for simplicity, as used herein it should be understood that "stent" shall mean both a stent or a stent graft) 63 is shown compressed onto the central catheter shaft 61. The self expanding stent 63 is constrained in the compressed state by a flexible sheath 65. The sheath 65 can be activated by a pull line (not shown) releasing a series of "slip-knots" that allow the sheath to split open and release the self expanding stent. The two guidewire tubes 67, 69 are passed through two side-branch openings in the stent 63 and also pass through two openings within the flexible sheath 65. The openings in the flexible sheath can be configured, for example, as slits propagating to the seam line of the flexible sheath.

The three guidewires 34, 36, 38 (from FIG. 4, emanating from the proximal hub assembly 58) are shown being "back-loaded" into the three guidewire lumens 62, 64, 66 within the stent delivery system 60, in the direction depicted by the arrows 73.

Figure 6:
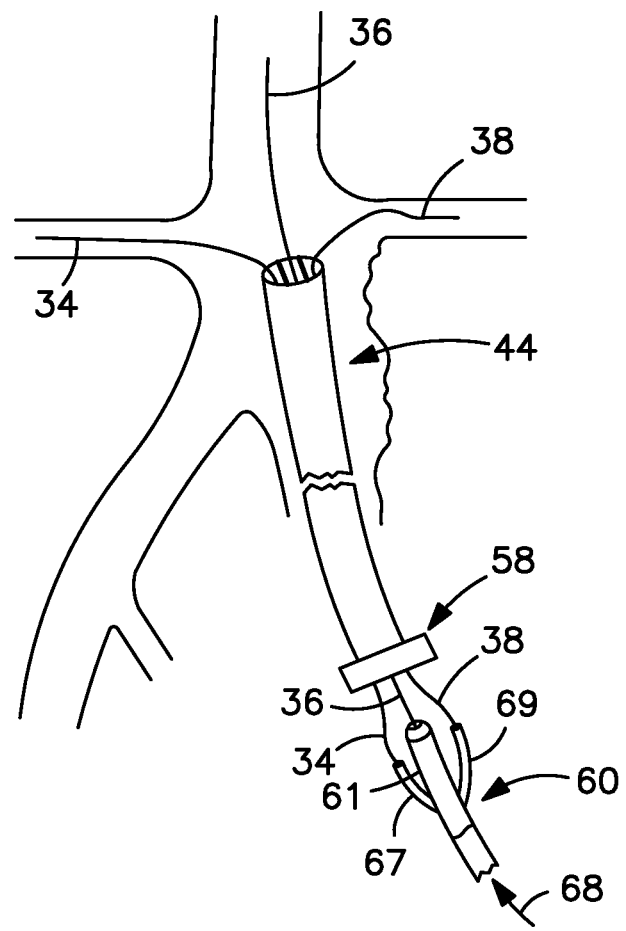
FIG. 6 shows a perspective view of an introducer sheath 44 of the present invention. Shown is the distal end of the stent delivery system being advanced toward the proximal hub assembly.

FIG. 6 shows a perspective view of an introducer sheath 44 of the present invention. Two guidewires 34, 38 are shown back-loaded into the stent delivery system tubes 67, 69. The third guidewire 36 is shown back-loaded into the guidewire lumen within the central catheter shaft 61. Shown is the distal end of the stent delivery system 60 being advanced in the direction 68 toward the proximal hub assembly 58.

Figure 7:
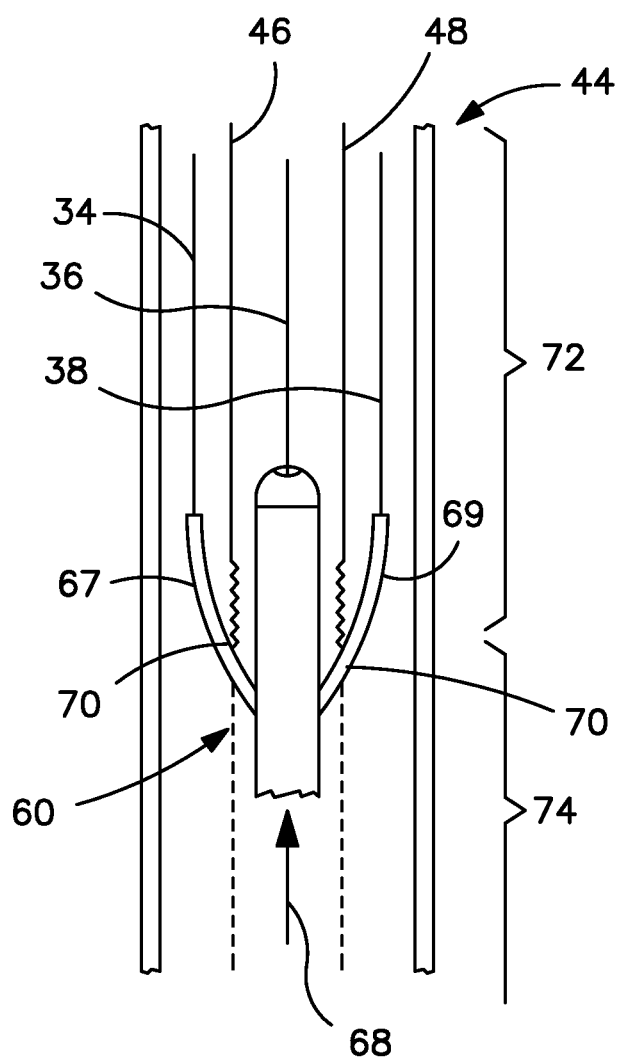
FIG. 7 is a partial cross-sectional view of an introducer sheath with two disruptable barriers. The barriers are shown being ripped, deformed or in other words "disrupted" to form a single lumen within the introducer sheath.

Shown in FIG. 7 is a partial cross-sectional view of an introducer sheath 44 according to the present invention. A distal end of a stent delivery system 60 has been inserted through the proximal hub assembly 58 (see FIG. 6) and is being advanced distally in the direction depicted by arrow 68. In portion 72, the three guidewires 34, 36 and 38 are separated by the disruptable barriers 46 and 48. As the stent delivery system 60 is advanced, the barriers 46 and 48 tear, rip, deform or in other words "disrupt" 70, thereby forming a single lumen within the introducer sheath portion 74.

The term "disruptable barrier" is defined as a member that creates at least two lumens within a catheter shaft and is tailored to allow conversion to a fewer number of lumens. For example a pair of disruptable barriers can create three separate lumens that are then transformed into less than three lumens. Similarly, flexible partitions or walls within a catheter can initially form several lumens (for example four) that are subsequently converted into less than four lumens. A disruptable barrier (or barriers) therefore provides a means to prevent entanglement of at least two guidewires, while also allowing the subsequent advancement of a medical device along the guidewires. In an aspect of the invention, a disruptable barrier (or barriers) provides a means to isolate and prevent entanglement of at least two guidewires, while also allowing the subsequent advancement of a medical device along the guidewires.

Figure 8:
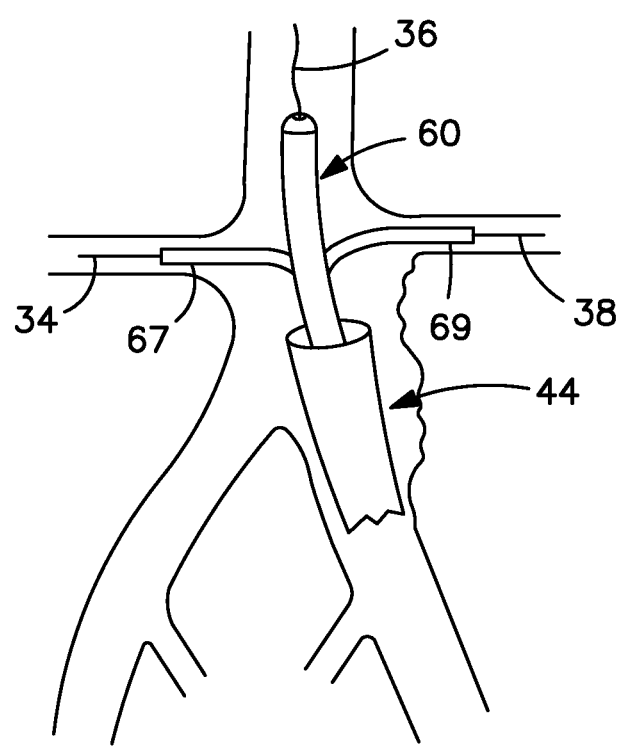
FIG. 8 is a partial perspective view of an introducer sheath that has been fully "converted" or "transformed" into a single lumen catheter by the disruption of the two internal barriers.

FIG. 8 is a schematic representation of an aortic section with a partial perspective view of an introducer sheath 44 according to the present invention. Shown is the distal end of a stent delivery system 60 projecting from the distal end of the introducer sheath 44. The introducer sheath 44 has been fully "converted" or "transformed" into a single lumen catheter by the disruption of the two internal barriers (46, 48 FIG. 2A). Also shown are three guidewires 34, 36 and 38 located within the aorta and within two renal arteries. The three guidewires are contained within the stent delivery system guidewire lumens (62, 64 and 66 of FIG. 5).

Figure 9:
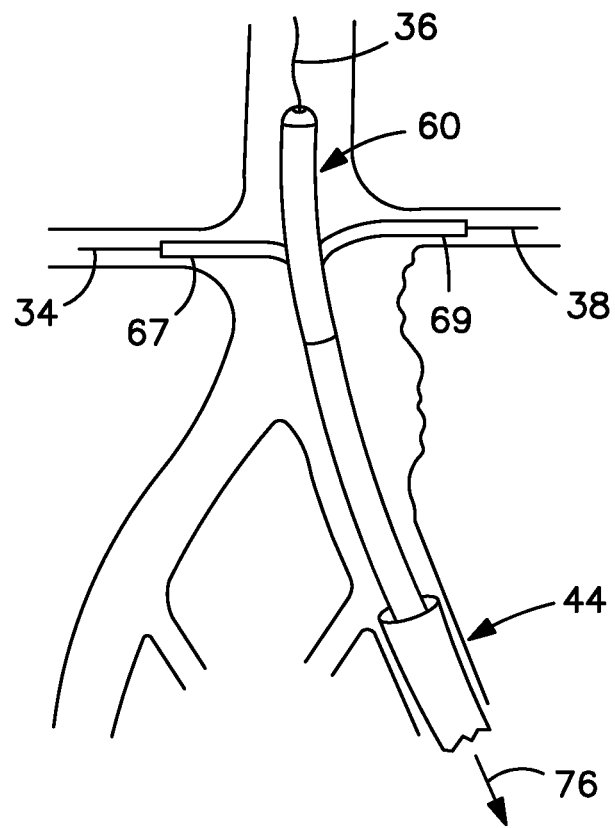
FIG. 9 is a partial perspective view of a stent delivery system along with an introducer sheath according to the present invention. Shown is the introducer sheath being partially withdrawn to fully expose the constrained self-expanding stent portion of the delivery system.

FIG. 9 is a schematic representation of an aortic section with a partial perspective view of a stent delivery system 60 along with an introducer sheath 44 according to the present invention. Shown is the introducer sheath 44 being partially withdrawn from the distal end of the stent delivery system 60, in the direction depicted by arrow 76. The sheath 44 is partially withdrawn to fully expose the constrained self-expanding stent portion of the delivery system 60.

Figure 10:
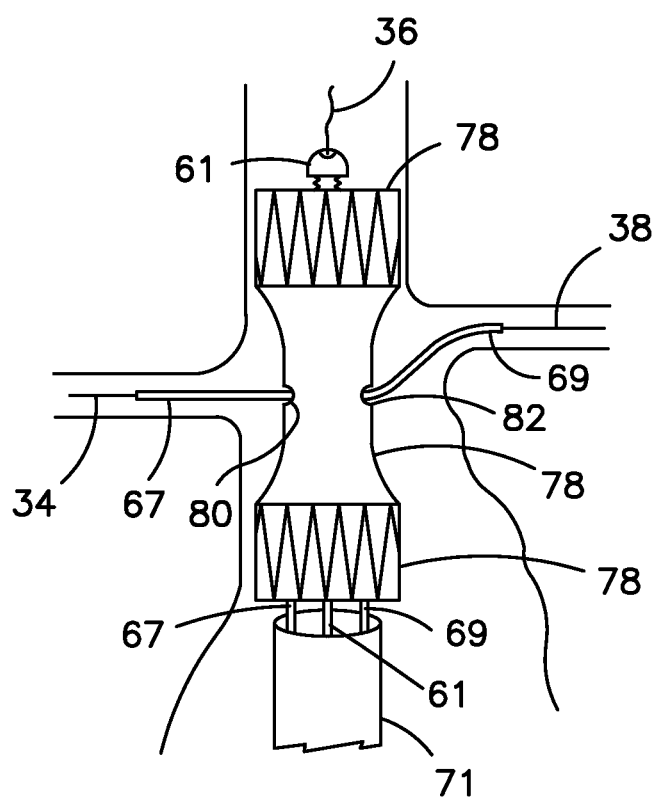
FIG. 10 is a schematic representation of an aortic section with a partial perspective view of a stent delivery system. Shown is a first or "main body" stent after deployment.

FIG. 10 is a schematic representation of an aortic section with a partial perspective view of a stent delivery system. Shown is a first or "main body" stent 78 after deployment. In a preferred embodiment the main body stent is self-expanding and has appropriate side hole openings 80 and 82 that roughly align to the side branch arteries to be subsequently stented. The main body stent 78 is compacted into the stent delivery system 60 (FIG. 9) with the two guidewire tubes 67, 69 and two side branch guidewires 34, 38 pre-routed through the appropriate side holes or ports in the main body stent. Thus when deployed, the two side branch guidewires 34, 38 remain within the target vessels and are pre-routed through the side ports in the main body stent. The flexible sheath (FIG. 5, item 65) has been omitted for clarity.

Figure 11:
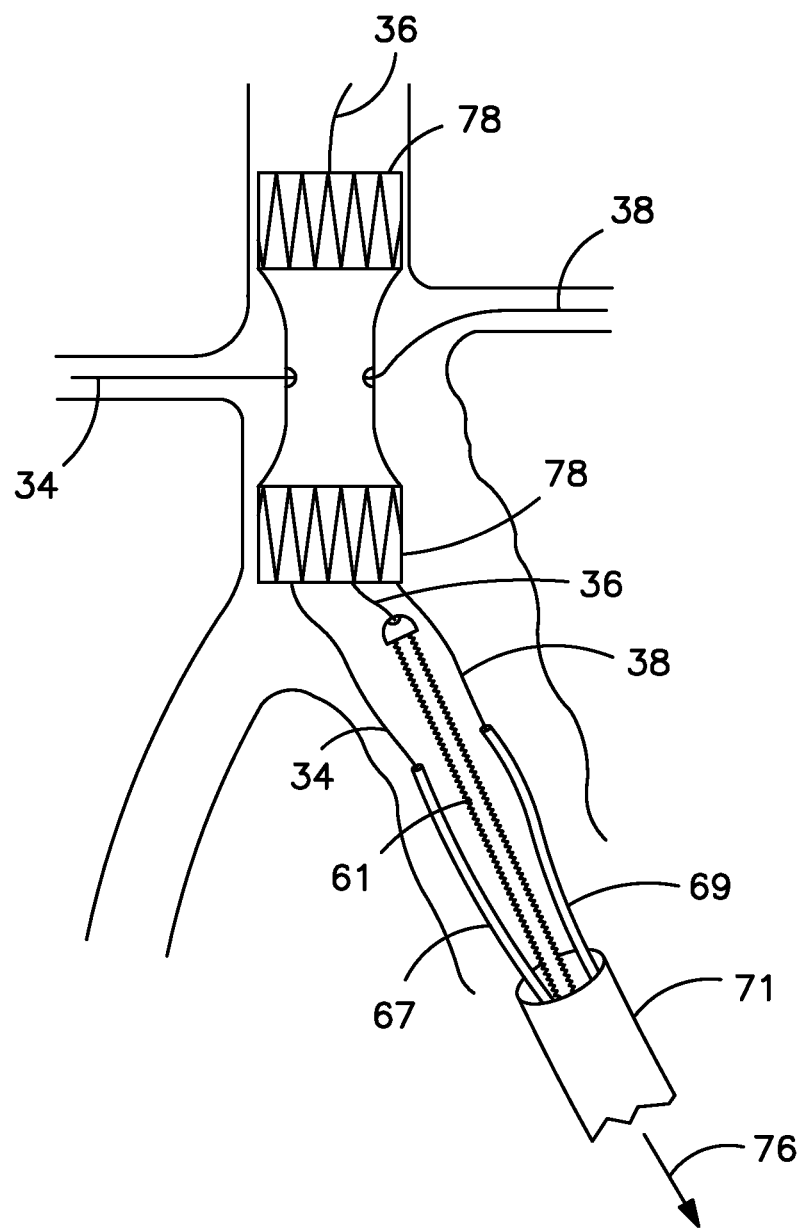
FIG. 11 is a schematic representation of an aortic section with a perspective view of a deployed main body stent. Shown are two guidewires within the targeted renal arteries that pass through two side ports within the wall of the deployed main body stent.

FIG. 11 is a schematic representation of an aortic section with a perspective view of a deployed main body stent 78. Shown are two guidewires 34, 38 within the targeted renal arteries that pass through two side ports 80, 82 within the wall of the deployed main body stent 78. Shown is the central shaft 61 of the stent delivery system (60, FIG. 9) being withdrawn along with the two guidewire tubes 67, 69 and the catheter shaft 71, in the direction depicted by arrow 76. The three guidewires 34, 36, 38 remain in their target vessels.

Figure 12:
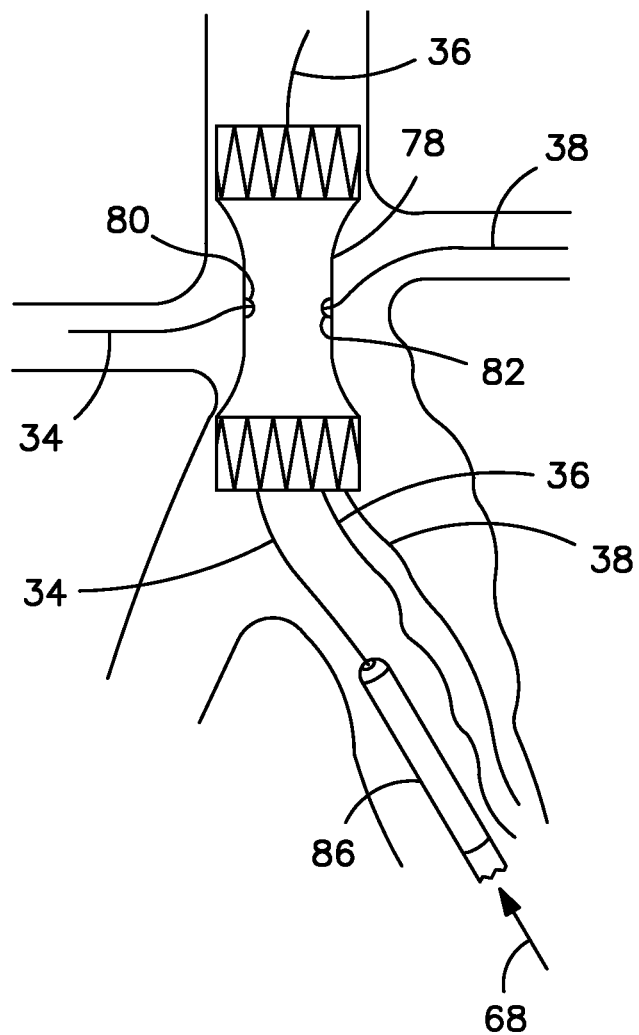
FIG. 12 is a schematic representation of an aortic section with a perspective view of a deployed main body stent. Shown is a first side-branch stent delivery system being advanced over the first guidewire 34.

Shown in FIG. 12 is a schematic representation of an aortic section with a perspective view of a deployed main body stent 78. Shown is a first side-branch stent delivery system 86 being advanced over the first guidewire 34, in the direction indicated by arrow 68. The side-branch stent can be self expanding and constrained by a sheath in a manner similar to that of the main body stent of FIG. 5.

Figure 13:
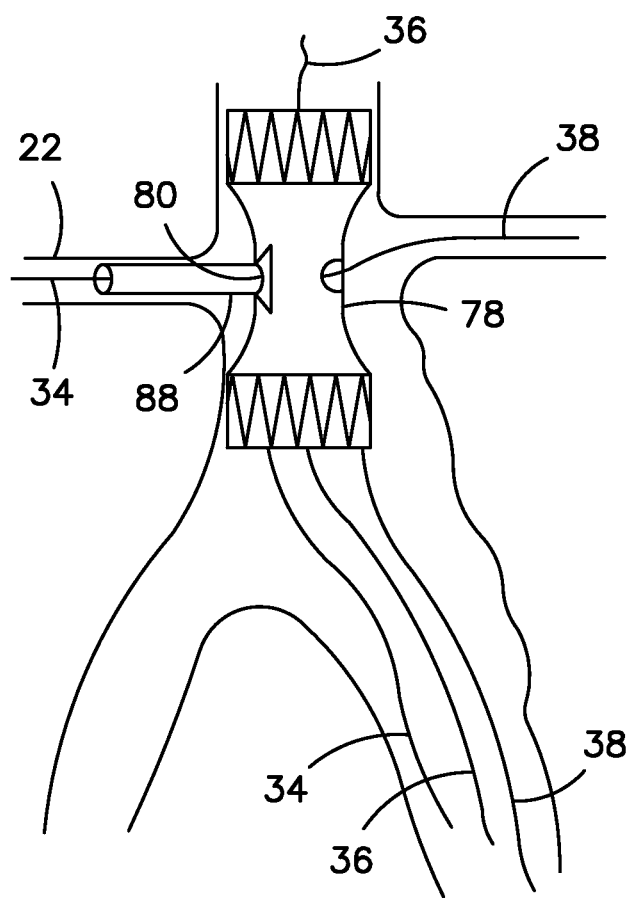
FIG. 13 is a schematic representation of an aortic section with a perspective view of a deployed main body stent. Shown is a first side branch stent that has been deployed into the right renal artery.

Shown in FIG. 13 is a schematic representation of an aortic section with a perspective view of a deployed main body stent 78. Shown is a first side branch stent 88 that has been deployed into the right renal artery 22. The first side branch stent 88 has been deployed through the first side branch port 80 creating a seal between the main body stent 78 and the first side branch stent 88.

Figure 14A:
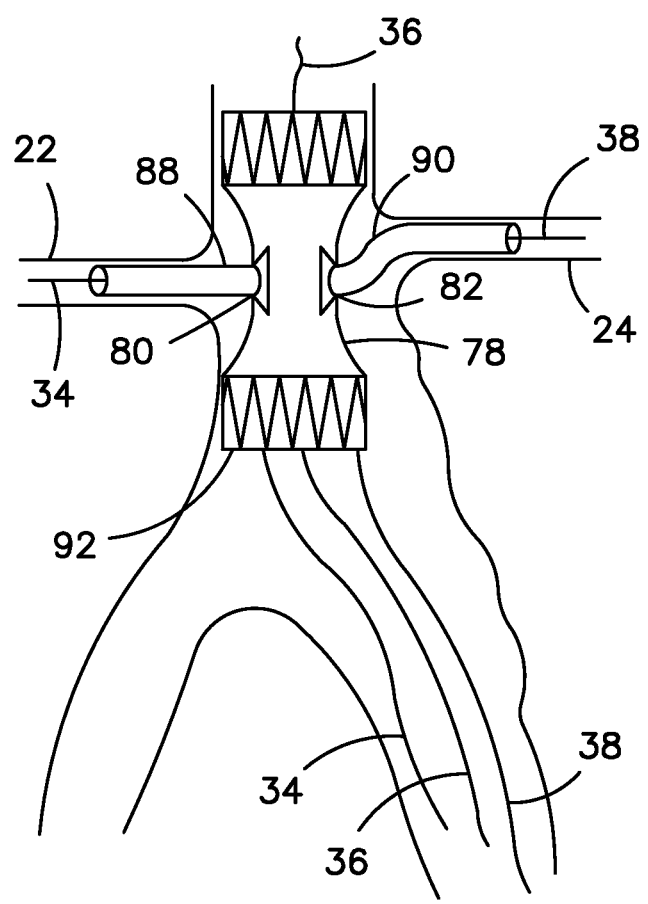
FIG. 14A is a schematic representation of an aortic section with a perspective view of a deployed main body stent. Shown is a second side branch stent that has been deployed into the left renal artery.
Figure 14B:
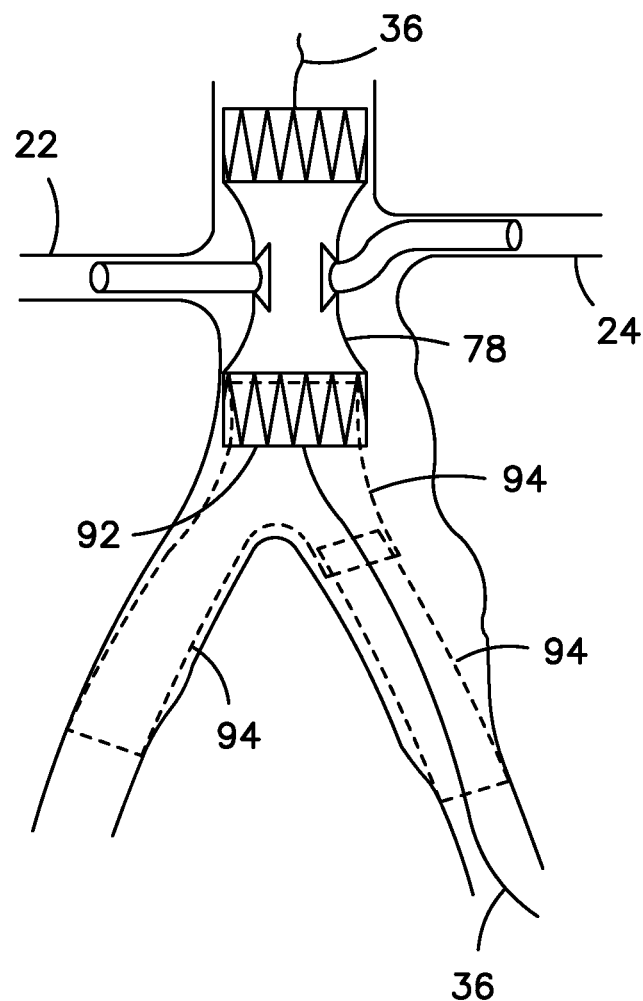
FIG. 14B is a schematic representation of an aortic section with a perspective view of a deployed main body stent and two attached side-branch stents. Also shown is a dashed profile of a bifurcated intraluminal device engaged into the main body stent.

Shown in FIG. 14 A is a schematic representation of an aortic section with a perspective view of a deployed main body stent 78. Shown is a second side branch stent 90 that has been deployed into the left renal artery 24. The second side branch stent 90 has been deployed through the second side branch port 82 creating a seal between the main body stent 78 and the second side branch stent 90.

The existing guidewire placements can be subsequently used for additional diagnostics or repairs (such as ballooning or stent placement). Additional repair or diagnostic devices can include but are not limited to bifurcated stent grafts, single lumen tube grafts, combinations of modular graft components, radiographic injection devices, embolic filters, occlusion, anchoring or seating balloons, fixation or anchoring devices and endoscopes. In a preferred example the two side-branch guidewires 34, 38 can be withdrawn and an additional device (or devices) can be advanced along the central guidewire 36. When at the desired location subsequent devices can be released and engaged to the "docking" portion 92 of the main body stent 78 forming a complete repair of the aneurysmal site.

For example, shown in FIG. 14 B is a schematic representation of an aortic section with a perspective view of a deployed main body stent 78 and two attached side-branch stents. Also shown is a dashed profile of a bifurcated intraluminal device 94 engaged into the docking portion 92 of the main body stent 78.

As shown in FIG. 14 A, the stents 78, 88, 90 can be balloon expandable, self expanding or both. Self expanding stents can be further "seated" with a balloon if desired, using the appropriate guidewire or guidewires. The side ports 80 and 82 in the main body stent 78 can incorporate side branch stent sealing features such as conical interfaces, support frames, compliant surfaces etc. that enhance or maintain an effective seal between the stents. Side branch stents 88 and 90 can similarly incorporate sealing features.

Although depicted in a renal/aortic repair procedure, the devices and methods of the present invention can be used in other repair procedures involving branched vessels. Anchoring balloons can also be incorporated into the various guidewires to help maintain the guidewire positions during the repair procedure.

During the insertion of an introducer sheath of the present invention a "split" dilator can be used in a normal fashion. Such a split dilator has longitudinal slits or separate stiffening portions that are tailored to slip into the individual lumens of the introducer sheath of the present invention.

The disruption or tearing of the barrier or barriers of the present invention can be initiated, for example, with the use of a "slitting tool". Such a slitting tool can be partially inserted into the introducer sheath of the present invention prior to the back loading of the first stent device. The slitting tool can initiate the disruption or separation of the barrier/s and can then be removed prior to the device insertion. Similarly, the distal tip of the first stent device can incorporate a barrier "disrupting" feature such as a sharp or fluted surface. Also, the barrier can be of a material that will tear as a relatively blunt distal tip of a catheter is advanced.

Figure 15A:
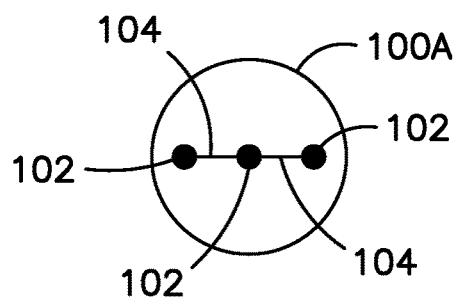
FIGS. 15A through 15C are top plane views of three hemostatic sealing disks that incorporate pre-punctured guidewire insertion sites and pre-slit device insertion slots.
Figure 15B:
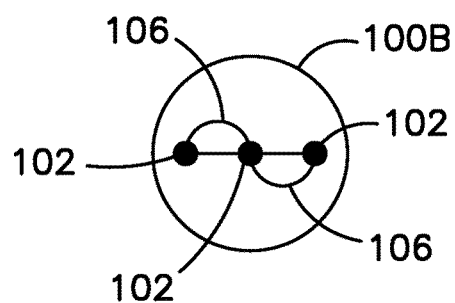
Figure 15C:
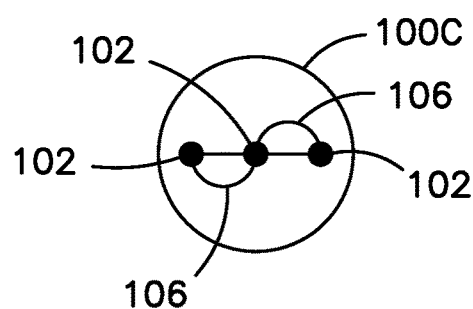
Figure 16:
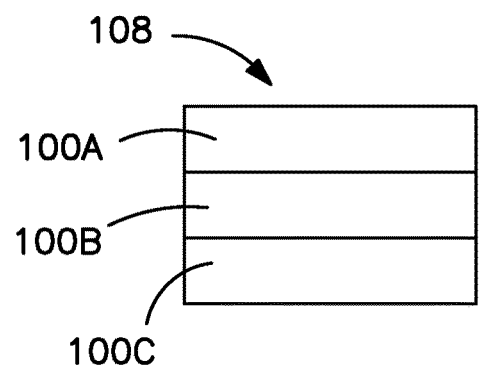
FIG. 16 is a side view of three sealing disks aligned and stacked to form a hemostatic sealing disk assembly.

When multiple guidewires are used with an introducer sheath, an effective hemostatic seal within the proximal hub assembly (FIG. 6, item 58) is desirable to minimize back-bleeding. Elastomeric sealing disks can be incorporated into a proximal hub assembly (FIG. 6, item 58) that are configured to allow the insertion of multiple guidewires followed by the insertion of a larger device or delivery system. Shown in FIG. 15A through 15C are top plane views of three sealing disks 100A, 100B, 100C that incorporate pre-punctured guidewire insertion sites 102. The guidewire insertion sites can be interconnected to allow for the formation of one orifice for the subsequent advancement of a larger device or delivery system. For example, shown are pre-punctured guidewire insertion sites 102 interconnected by linear pre-slit device insertion features 104, or interconnected by curved pre-slit device insertion features 106. The seals can also incorporate "rip able" sections that readily separate or tear as an alternative to pre-slit insertion features. Multiple sealing disks can then be aligned and stacked together within the hub assembly to form an effective guidewire or device hemostatic seal. Shown in FIG. 16 is a side view of three sealing disks 100A, 100B, 100C aligned and stacked to form a sealing disk assembly 108.

Disruptable barriers of the present invention can have various configurations. Shown for example in FIG. 17A is an end view of a multi-lumen catheter 110A having first, second and third lumens 112, 114, 116. The multi-lumen catheter 110A can be expanded (for example by the insertion of a device delivery system) to form a single lumen 118 within the catheter as shown in end view, FIG. 17B. Thus the barriers of FIG. 17A "disrupt" to form a catheter with fewer lumens. Suitable materials for use as disruptable barriers include, but are not limited to, polyethylene, polypropylene, polyvinyl chloride, polyurethanes, siloxanes, polyetherester, polytetrafluoroethylene, polyimide, nylon, polyethylene terephthalate, thermoplastic elastomers, polyolefins, polyester, polyamides, polydimethylsiloxane, natural rubber, polyether block amide (PEBAX), ethylene vinyl acetate, and combinations thereof.

Similarly, FIGS. 18A through 18C depict catheters with interior barriers that can be disrupted to form fewer lumens. Shown in FIG. 18A is an end view of a catheter 120A with two disruptable barriers 122 that form first and second lumens 112, 114. Shown in FIG. 18B is an end view of a catheter 120B with three disruptable barriers 122 that form first, second and third lumens 112, 114, 116.

Shown in FIG. 18C is an end view of a catheter 120C with four disruptable barriers 122 that form first, second, third and fourth lumens 112, 114, 116, 117. In these embodiments the barriers can be disrupted by pushing a device (or devices) distally along guide wire(s) previously located in the lumens. The barriers can be disrupted by being pushed aside as the device is advanced along the guide wire.

Other configurations of the present invention, similar to that of FIG. 17A, are configured with disruptable barriers. Shown for example in FIG. 19A is an end view of a catheter 124A having two lumens 112, 114 that will transform into a single lumen catheter when expanded. Shown in FIG. 19B is an end view of a catheter 124B having three lumens 112, 114, 116 that will transform into a single lumen catheter when expanded.

Shown in FIG. 20 is an end view of a further embodiment of the present invention. Shown is an end view of a catheter 126 having four disruptable membranes 122 that form three lumens 112, 114, 116. The three lumens can be converted into a single lumen when expanded. Or, as discussed above, the lumens can be converted into a single lumen by being pushed aside by a suitable device (or devices) as the device(s) is advanced along guidewire(s) previously located in the lumens.

Shown in FIG. 21 is an end view of an alternate embodiment of the present invention. Shown is an end view of a catheter 130 having two disruptable barriers 131 that form three lumens 112, 114, 116. Guidewires are advanced and retained in these flexible cylindrical lumens internally tangent to the inner surface of the catheter. Each barrier can have a slit (or other longitudinal opening) that can release the guidewires as a delivery catheter is advanced distally through catheter 130.

Various cross-sectional profiles according to the present invention can be extruded, formed by wrapping or windings, or be comprised of multiple sections laminated or bonded together. The initial number of lumens can include but are not limited to two, three, four, five, six, seven, eight, nine or ten or more lumens. These multi-lumen catheters can be converted, according to the present invention, into "fewer than the initial number of lumens" which includes but is not limited to one, two, three, four, five, six, seven, eight, nine or ten or more lumens.

A catheter or introducer sheath having two disruptable barriers that are "rip able", "slit able" or tear able can be fabricated by providing, for example, a three piece mandrel having a general cross-section or end view according to FIG. 2B. A tubular member that has relatively high longitudinal strength but with relatively low radial strength can be placed around the center section of the three piece mandrel, forming an assembly. The assembly can then be wrapped with an adhesive coated film or constrained by an adhesive coated tube. After adhesive curing, the mandrel sections can be removed producing a catheter having the general cross-sectional profile as shown in FIGS. 2A and 2B. The outer wall of the catheter is therefore formed by the film wrap or tubular constraint. The two disruptable, (e.g., "rip able", "slit able", or tear able) barriers are formed from the tubular member. The low radial strength of the tubular member allows for the tubular member to be readily slit along its longitudinal axis. Suitable materials for use as rip able, slit able, or tear able barriers include, but are not limited to, polyethylene, polypropylene, polyvinyl chloride, polyurethane, siloxanes, polyetherester, polytetrafluoroethylene, polyimide, nylon, polyethylene terephthalate, thermoplastic elastomers, polyolefins, polyester, polyamides, polydimethylsiloxane, natural rubber, polyether block amide (PEBAX), and ethylene vinyl acetate, and combinations thereof.

As an alternative to the concept of "disruptable barriers" modified "dilators" used in conjunction with introducer sheaths can be used to minimize or prevent the occurrence of crossed or entangled guidewires. The dilator has a length, a proximal end, and a distal end, the dilator is sized to be locatable within the lumen of an introducer sheath. The introducer sheath has a length, a proximal end, a distal end, and a lumen extending from the proximal end to the distal end. The dilator is further defined as having an outer geometric shape that defines at least two lumens between the introducer sheath and the dilator when the dilator is inserted into the introducer sheath lumen. Moreover, the dilator can comprise at least one lumen defined by an inner surface of the dilator.

Figure 22:
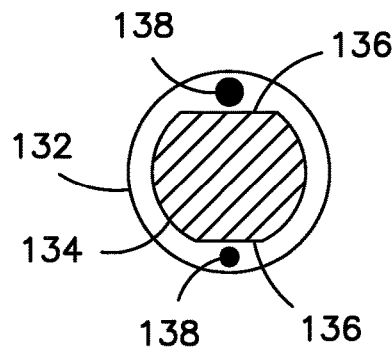
FIG. 22 is an end cross-sectional view of an introducer sheath surrounding a dilator that has two flat surfaces. The clearance space between the introducer sheath and the dilator flat surfaces form two guidewire lumens.

For example, a dilator can have two opposing flat surfaces extending along its length. When inserted into the mating introducer sheath, the flat surfaces form two guidewire lumens between the dilator and the inner wall of the introducer sheath. When the guidewires are positioned into the desired target site the dilator can be removed and a delivery system can then be back-loaded onto the guidewires and advanced through the introducer sheath. The proximal guidewire positions can be maintained by suitable fixation at the hub assembly. Shown in FIG. 22 is an end cross-sectional view of an introducer sheath 132 surrounding a dilator 134 that has two flat surfaces 136. The clearance space between the introducer sheath 132 and the dilator flat surfaces 136 form two guidewire lumens. Shown are two guidewires 138 positioned within the clearance space between the introducer sheath 132 and the dilator flat surfaces 136. Clearances between the introducer sheath 132 and dilator 134 have been exaggerated for clarity.

Figure 23:
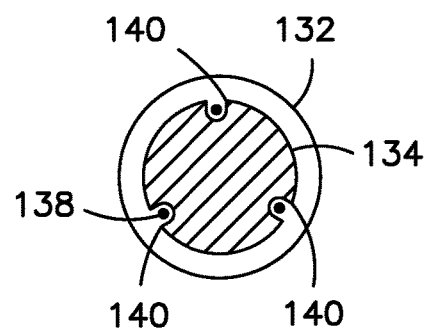
FIG. 23 is an end cross-sectional view of an introducer sheath surrounding a dilator that has three guidewire grooves.
Figure 24:
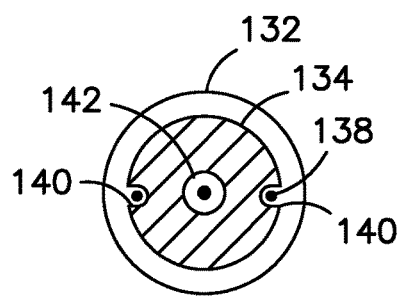
FIG. 24 is an end cross-sectional view of an introducer sheath surrounding a dilator that has two guidewire grooves and a central lumen.

Shown in FIG. 23 is an alternate dilator according to the present invention. Shown is an end cross-sectional view of an introducer sheath 132 surrounding a dilator 134 that has three guidewire grooves 140. Similarly, shown in FIG. 24 is an end cross-sectional view of an introducer sheath 132 surrounding a dilator 134 that has two guidewire grooves 140 and a central lumen 142, formed by the inner surface of the dilator.

Figure 25:
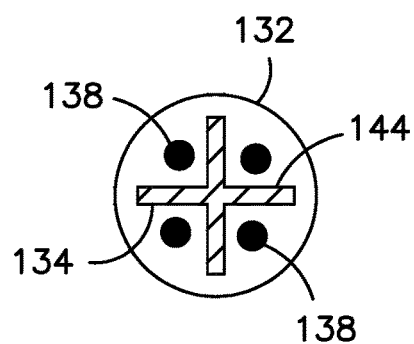
FIG. 25 is an end cross-sectional view of an introducer sheath surrounding a dilator that has a "cross-shaped" profile that forms four lumens.

Shown in FIG. 25 is an alternate dilator according to the present invention. Shown is an end cross-sectional view of an introducer sheath 132 surrounding a dilator 134 that has a "cross-shaped" profile 144 that forms four lumens.

The modified dilators of the present invention therefore provide a "means to isolate and prevent entanglement of at least two guidewires" while also allowing the subsequent advancement of a medical device along the guidewires.

The specific configurations used to form separate guidewire lumens in the examples above can be embodied along the entire length of the dilator. Alternatively, the guidewire lumen features can be eliminated at the distal and/or proximal ends of the dilator. The elimination of the guidewire features for example at the distal end of the dilator allows a normal tapered tip of a dilator to extend from the introducer sheath during insertion. The dilator can then be further advanced into the introducer sheath to expose the distal guidewire lumens. The specific lumens of the present invention can be dimensioned to accept a variety of guidewire sizes or other devices. In any event, once the guidewires are advanced through the lumens and located at the desired treatment sites, the dilator can be removed from the introducer sheath lumen to allow for the advancement of the desired device(s) over the guidewires. The concepts of disruptable barriers can be combined with dilators modified to incorporate guidewire lumens. In addition the distal end of an introducer sheath can have staggered and/or angulated exit ports for the guidewires or other devices.

Figure 26:
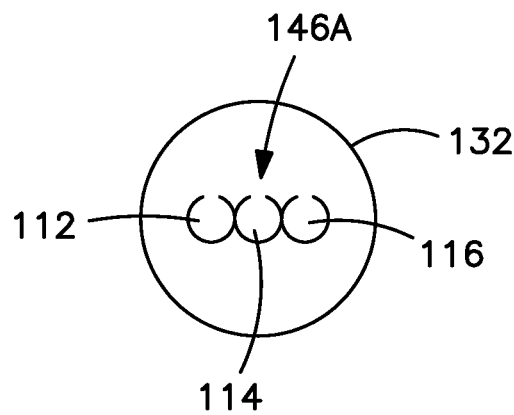
FIGS. 26 and 27 are cross-sectional end views of guidewire positioning catheters surrounded by an introducer sheath. The guidewire positioning catheter has three guidewire lumens each having a longitudinal slit or opening. The slit or opening allows the guidewires to be released as a subsequent delivery system is advanced through the introducer sheath.
Figure 27:
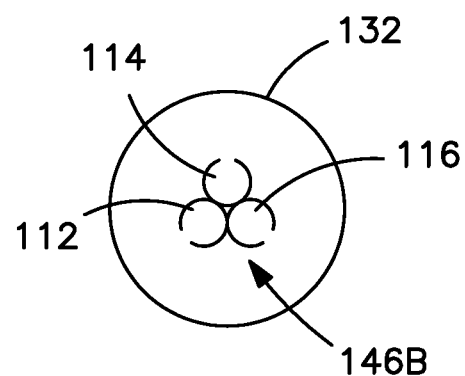

Shown in FIGS. 26 and 27 are cross-sectional end views of guidewire positioning catheters 146A-B surrounded by an introducer sheath 132. As shown in FIGS. 26 and 27, the guidewire positioning catheter 146A-B has three guidewire lumens 112, 114, 116 each having a longitudinal slit or opening. The slit or opening allows the guidewires to be released as a subsequent delivery system is advanced through the introducer sheath.

The guidewire positioning catheters of the present invention therefore provide a means to isolate and prevent entanglement of at least two guidewires while also allowing the subsequent advancement of a medical device along the guidewires.

A method of the present invention can include the following steps:
A) provide an introducer sheath and a matching dilator system that provides a means to prevent entanglement of at least two guidewires;
B) insert and locate the introducer sheath approximate to a desired target site;
C) insert and locate at least two guidewires within the introducer sheath;
D) back-load a medical device onto the at least two guidewires; and
E) advance the medical device over the at least two guidewires through the introducer sheath to the desired target site.

The means to prevent entanglement of at least two guidewires can include the incorporation of at least one disruptable barrier within the introducer sheath. Additional means to prevent entanglement of at least two guidewires can include, but are not limited to, the incorporation of at least two guidewire lumens into the dilator or by the use of a guidewire positioning catheter.

While particular embodiments of the present invention have been illustrated and described above, the present invention should not be limited to such particular illustrations and descriptions. It should be apparent that changes and modifications may be incorporated and embodied as part of the present invention within the scope of the following claims.

We claim:

1. A method of manufacturing an introducer sheath, said method comprising:
providing a mandrel extending along a longitudinal axis thereof and having a cylindrical outer surface, the mandrel having at least first and second sections each extending along the longitudinal axis;
placing a film tubular member around one of the at least first and second sections of the mandrel;
sandwiching a portion of the tubular member between the at least first and second sections, the portion of the tubular member defining a disruptable barrier for the introducer sheath;

extending a film layer about each section of the mandrel such that the film layer surrounds the tubular member, the film layer having an adhesive facing the tubular member;

curing the adhesive to bond the film layer to the tubular member to form the introducer sheath with at least two lumens separated by the disruptable barrier; and removing the mandrel from the introducer sheath.

2. The method as set forth in claim 1, wherein each of the at least first and second mandrels include inwardly facing surfaces that engage to shape the disruptable barrier.

3. The method as set forth in claim 2, wherein the inwardly facing surfaces are planar.

4. The method as set forth in claim 3, wherein the inwardly facing surfaces are parallel.

5. The method as set forth in claim 1, wherein the tubular member comprises polytetrafluoroethylene.

6. The method as forth in claim 5, wherein the tubular member has relatively high longitudinal strength and relatively low radial strength.

7. The method as set forth in claim 1, wherein the disruptable barrier extends for substantially the entire length of the resulting introducer sheath.

8. The method as set forth in claim 1, wherein the mandrel includes longitudinally extending first, second and third sections having a collective cross section approximating a cross section of the introducer sheath.

9. The method as set forth in claim 8 including sandwiching opposite portions of the tubular member between opposite surfaces of the second section of the mandrel and the first and third sections of the mandrel to define first and second disruptable barriers, respectively.

10. The method as set forth in claim 9, wherein sides of the second section of the mandrel which do not sandwich the tubular member define portions of the outer surface of the mandrel.

11. The method as set forth in claim 10, wherein the opposite surfaces of the second section sandwiching the tubular member are planar.

12. The method as set forth in claim 11, wherein opposite surfaces of the second section sandwiching the tubular member are parallel.

13. The method as set forth in claim 9, wherein the first and second disruptable barriers extend for substantially the entire length of the resulting introducer sheath.

* * * * *